(12) United States Patent
Purcell

(10) Patent No.: US 11,382,578 B2
(45) Date of Patent: Jul. 12, 2022

(54) FLUORSCOPIC MARKERS FOR SINGLE VIEW POSITIONING

(71) Applicant: NeuroTronik IP Holding (Jersey) Limited, St. Helier (JE)

(72) Inventor: Scott Purcell, Raleigh, NC (US)

(73) Assignee: NuXcel Limited, Dublin (IE)

( * ) Notice: Subject to any disclaimer, the term of this patent is extended or adjusted under 35 U.S.C. 154(b) by 171 days.

(21) Appl. No.: 16/712,923

(22) Filed: Dec. 12, 2019

(65) Prior Publication Data

US 2020/0187879 A1 Jun. 18, 2020

Related U.S. Application Data

(60) Provisional application No. 62/778,350, filed on Dec. 12, 2018.

(51) Int. Cl.
*A61B 6/00* (2006.01)
*A61B 6/12* (2006.01)
*A61N 1/05* (2006.01)
*A61B 90/00* (2016.01)

(52) U.S. Cl.
CPC ............... *A61B 6/12* (2013.01); *A61B 6/485* (2013.01); *A61B 90/39* (2016.02); *A61N 1/05* (2013.01); *A61B 2090/3966* (2016.02); *A61B 2090/3983* (2016.02)

(58) Field of Classification Search
CPC ....................................................... A61B 6/12
See application file for complete search history.

(56) References Cited

U.S. PATENT DOCUMENTS

2014/0142590 A1* 5/2014 Masson .............. A61N 1/36128
606/129

* cited by examiner

*Primary Examiner* — Joseph M Santos Rodriguez

(57) ABSTRACT

An intravascular catheter includes an electrode carrying member. The catheter includes features visible in the fluoroscopic image that allow the practitioner to determine the radial position of the electrode carrying member within a blood vessel, and to confirm that the electrodes are positioned at the desired part of the vessel wall (e.g. against the posterior surface) and at the desired position along the length of the vessel, all without re-orienting the fluoroscope during the course of electrode positioning within the vascular. The features are shaped, formed in patterns, or possess other properties selected so that the appearance of the features on the fluoroscopic image differs depending on the rotational orientation of the electrodes. This can thus be used by the practitioner to determine whether, for example, an electrode carrying member having the features is positioned on the anterior or posterior wall of the blood vessel in which the array is positioned.

15 Claims, 5 Drawing Sheets

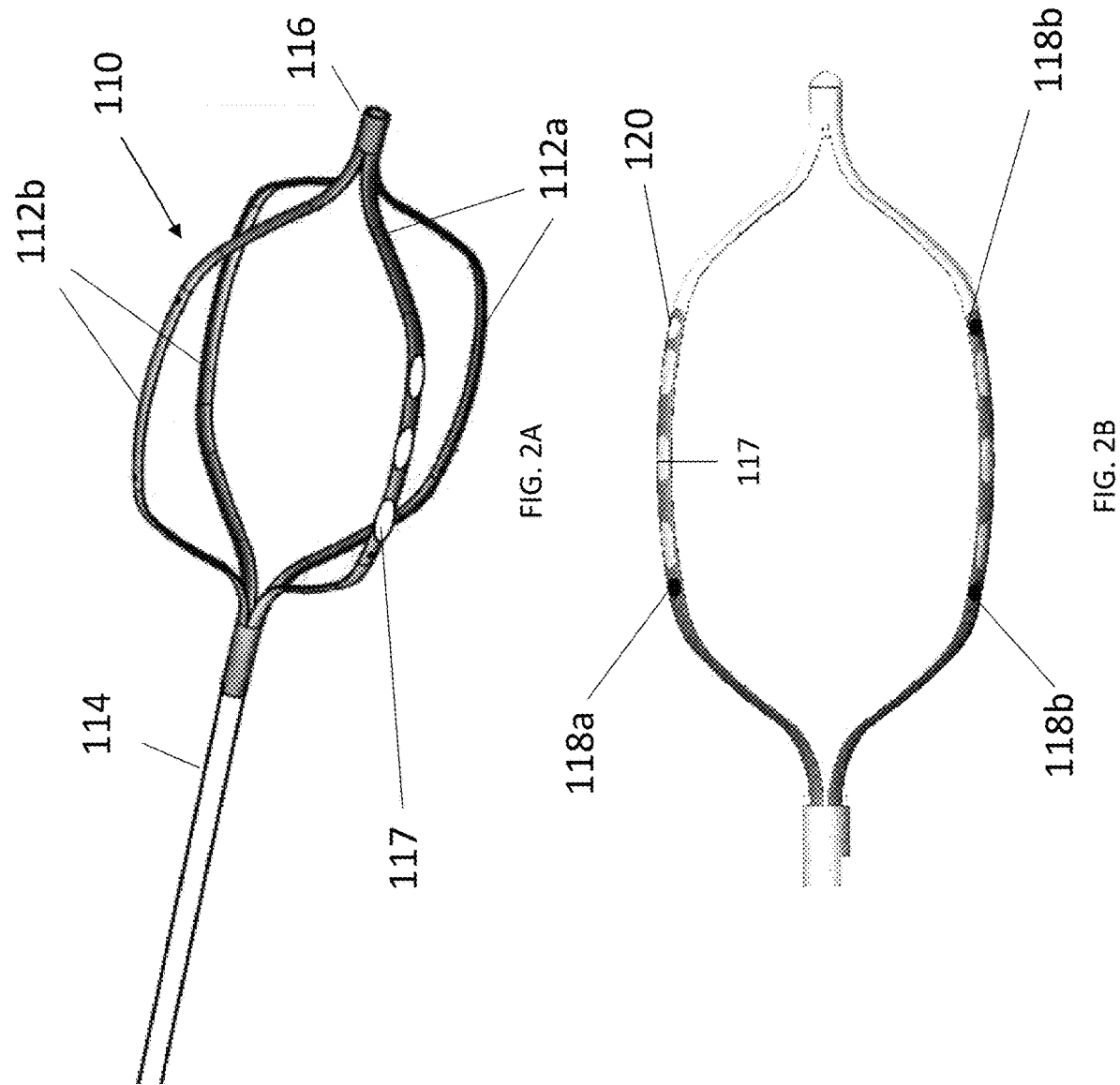

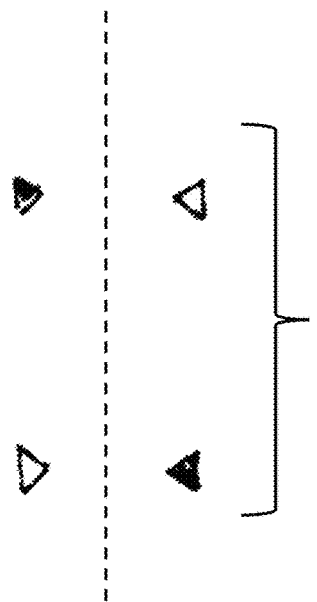
FIG. 2C
FIG. 2D
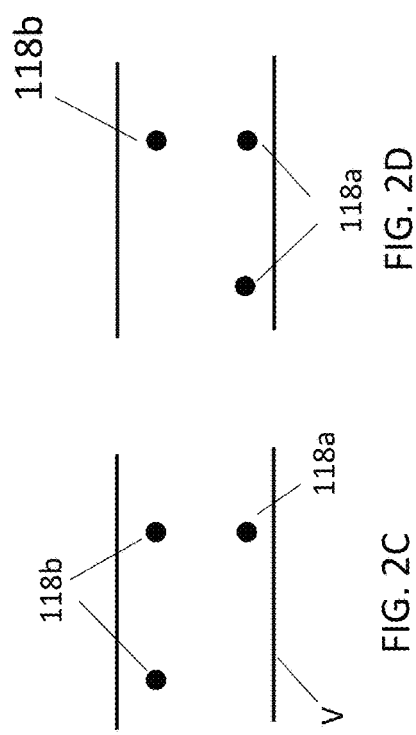
FIG. 3
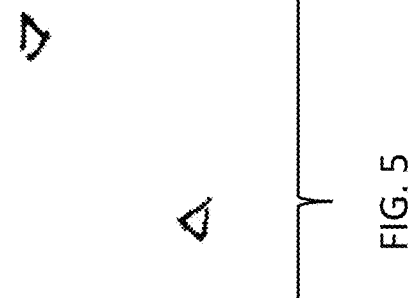
FIG. 5
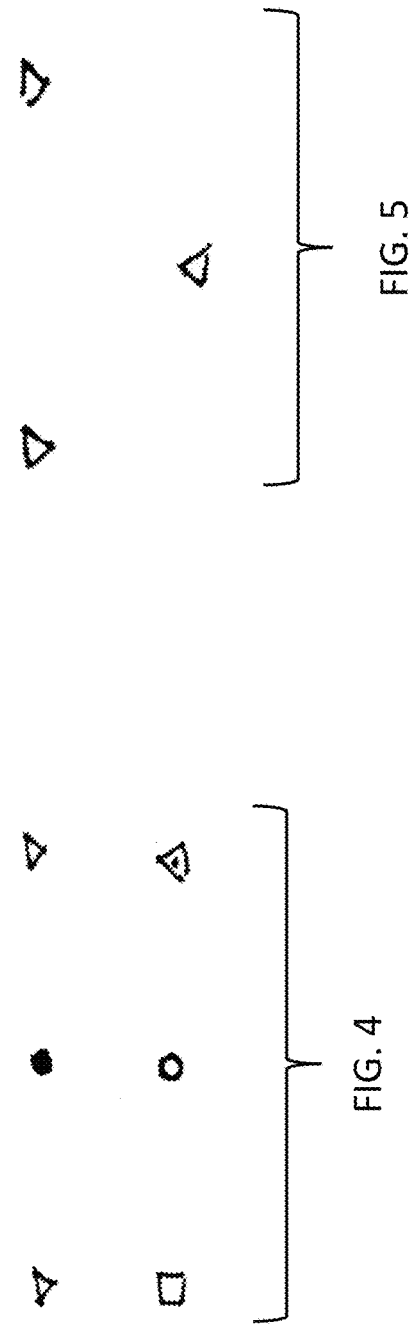
FIG. 4

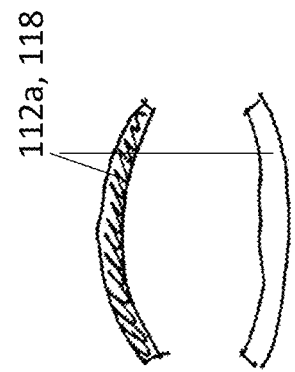
FIG. 6
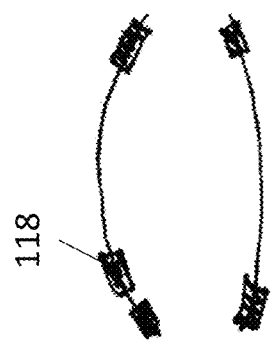
FIG. 7
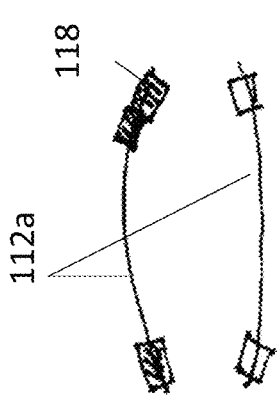
FIG. 9
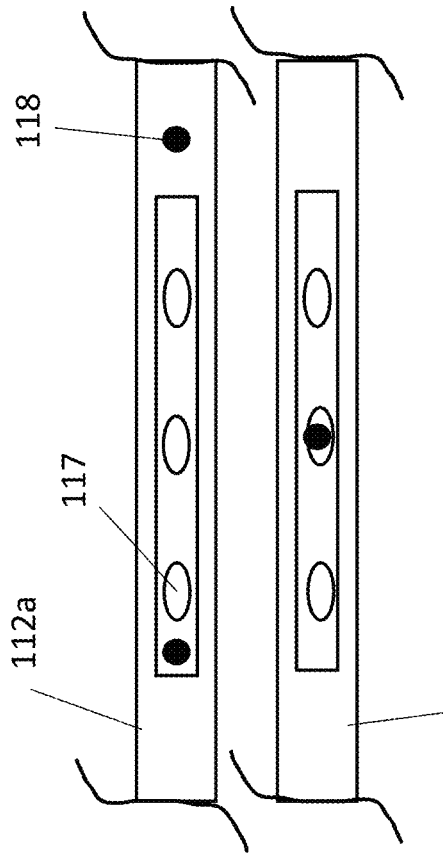
FIG. 8
FIG. 10
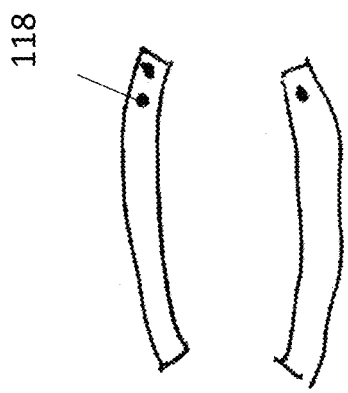

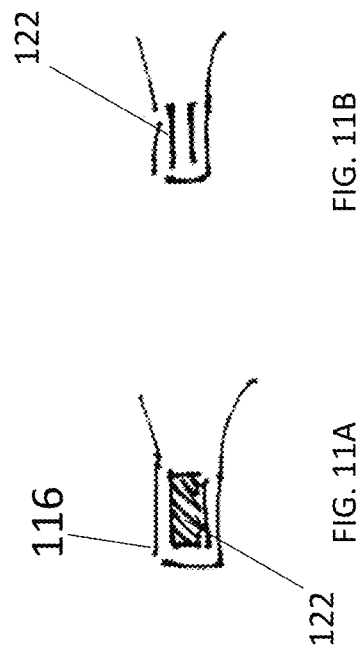
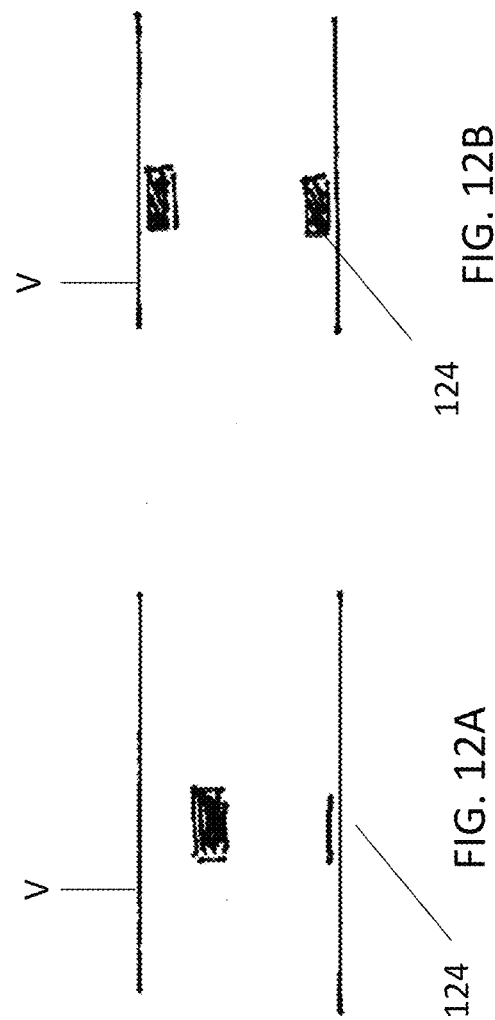

FLUORSCOPIC MARKERS FOR SINGLE VIEW POSITIONING

This application claims the benefit of US Provisional Application No. 62/778,350, filed Dec. 12, 2018.

TECHNICAL FIELD OF THE INVENTION

The present application generally relates electrodes for delivering energy or stimulus to tissue or structure of the body. More specifically, the application relates to fluoroscopically visible features or markers used by a practitioner to determine the orientation of an array of electrodes within a patient's body.

BACKGROUND

U.S. application Ser. No. 13/547,031 entitled System and Method for Acute Neuromodulation, filed Jul. 11, 2012 (the "'031 application"), filed by an entity engaged in research with the owner of the present application describes a system which may be used for hemodynamic control in the acute hospital care setting, by transvascularly directing therapeutic stimulus to parasympathetic nerves and/or sympathetic cardiac nerves using electrodes positioned in the superior vena cava (SVC). In disclosed embodiments, delivery of the parasympathetic and sympathetic therapy decreases the patient's heart rate (through the delivery of therapy to the parasympathetic nerves) and elevates or maintains the blood pressure (through the delivery of therapy to the cardiac sympathetic nerves) of the patient in treatment of heart failure.

US application Ser. Nos. U.S. Ser. No. 14/642,699 (the '699), filed Mar. 9, 2015 and U.S. Ser. No. 14/801,560 (the '560), filed Jul. 16, 2015, each incorporated by reference, describe transvascularly directing therapeutic stimulus to parasympathetic and/or sympathetic cardiac nerves using electrodes positioned in the SVC, right brachiocephalic vein, and/or left brachiocephalic vein and/or other sites. As with the system disclosed in the '031, the methods disclosed in these applications can decrease the patient's heart rate (through the delivery of therapy to the parasympathetic nerves) and elevate or maintain the blood pressure (through the delivery of therapy to the cardiac sympathetic nerves) of the patient in treatment of heart failure.

The '699 and '560 applications describe one form of catheter device that may be used to perform transvascular neuromodulation. In particular, these applications shows a support or electrode carrying member 10 of the type shown in FIG. 1 on the distal part of a catheter member 4. The electrode carrying member 10 includes a plurality of struts 12. One or more of the struts carries one or a plurality of electrodes 17. The electrode carrying member 10 is designed to bias such electrodes into contact with the vessel wall. The material forming the struts 12 may have a shape set or shape memory that aids in biasing the circumferentially-outward facing surfaces (and thus the electrodes) against the vessel wall.

U.S. Pat. No. 9,833,608, commonly owned with the present application, discloses that fluoroscopic imaging may be used to facilitate correct circumferential and longitudinal positioning of an array of this type, such as by allowing the practitioner to align radiopaque markers on the catheter with known anatomical landmarks.

The present application describes use of radiopaque markers or other features that allow the practitioner introducing the array into the vasculature to place the struts that have electrodes on them in the proper position and circumferential orientation within the blood vessel in order to reach the target nerve(s) with therapeutic energy delivered by the electrodes.

BRIEF DESCRIPTION OF THE DRAWINGS

FIG. 2A is a perspective view of a distal end of a neuromodulation catheter of a type described herein;

FIG. 2B is side elevation view of the distal part of the catheter of FIG. 2A, illustrating a marker arrangement for facilitating catheter positioning and orientation during visualization using a single fluoroscopic view;

FIG. 2C schematically depicts the arrangement of the marks on the catheter of FIGS. 2A and 2B as seen on the fluroscopic image (in this case the AP view) when the electrodes are positioned against the anterior wall of the target vessel V.

FIG. 2D schematically depicts the arrangement of the marks on the catheter of FIGS. 2A and 2B as seen on the fluroscopic image (in this case the AP view) when the electrodes are positioned against the posterior wall of the target vessel V.

FIG. 3 illustrates a second embodiment of a marker arrangement;

FIG. 4 illustrates a third embodiment of a marker arrangement;

FIG. 5 illustrates a fourth embodiment of a marker arrangement;

FIG. 6 illustrates a fifth embodiment of a marker arrangement;

FIG. 7 illustrates a sixth embodiment of a marker arrangement;

FIG. 8 illustrates a seventh embodiment of a marker arrangement;

FIG. 9 illustrates an eighth embodiment of a marker arrangement;

FIG. 10 illustrates a ninth embodiment of a marker arrangement;

FIG. 11A illustrates a tenth embodiment of a marker arrangement and shows the shape of the marker when the catheter is positioned in a first radial orientation and viewed on the fluoroscopic image;

FIG. 11B is similar to FIG. 11A but shows the shape of the marker when the catheter positioned in a second radial orientation and viewed on the fluoroscopic image;

FIG. 12A illustrates an eleventh embodiment of a marker arrangement and shows the view of the markers when the catheter is positioned in a first radial orientation and viewed on the fluoroscopic image.

FIG. 12B is similar to FIG. 12A but shows the view the markers when the catheter is positioned in a second radial orientation and viewed on the fluoroscopic image.

DETAILED DESCRIPTION

Figure 1:
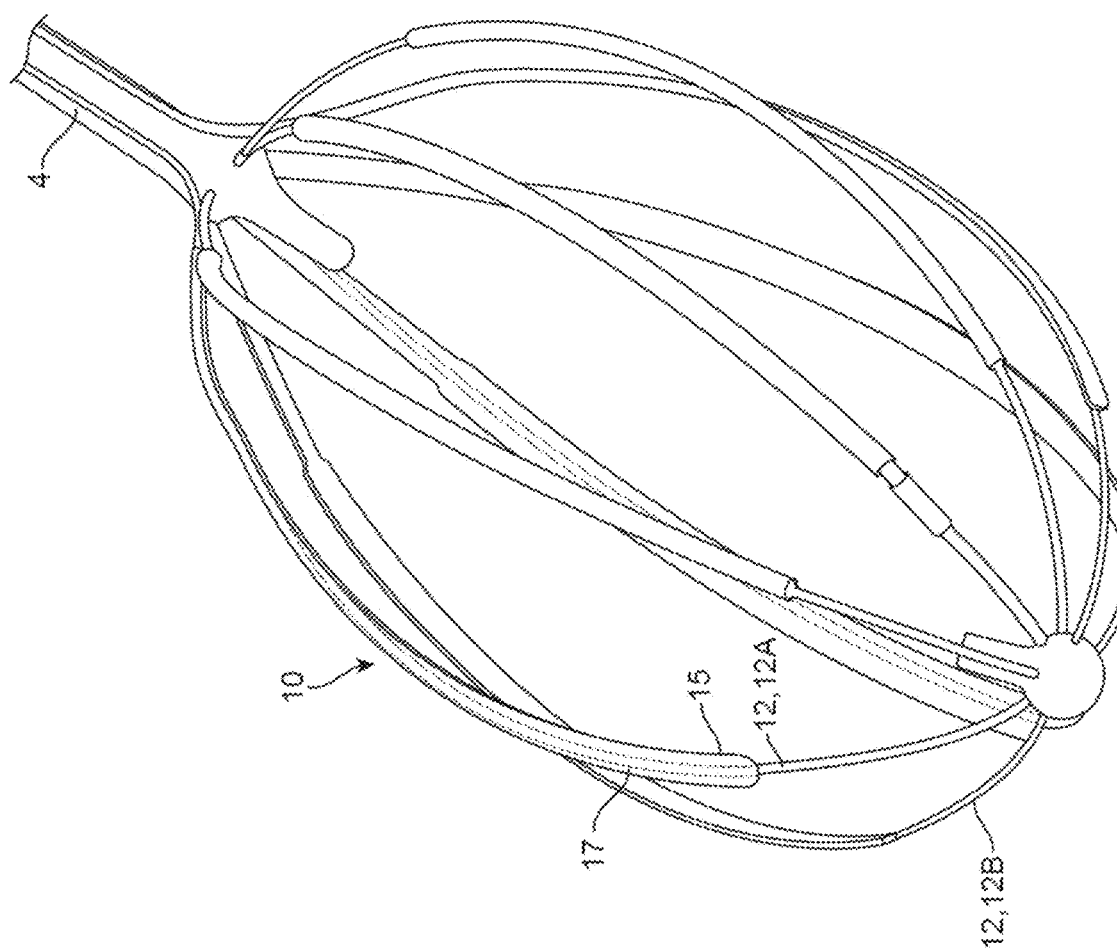
FIG. 1 is a perspective view of an electrode catheter of a type described in the prior art.

FIG. 2A shows one embodiment of an electrode catheter with which the fluoroscopically visible features described herein may be used. The electrode carrying member 110 is positioned on the distal part of a catheter member or shaft 114 and includes a plurality of struts 112a, 112b and a distal tip 116. Some or all of the struts carry one or more neuromodulation electrodes 117; these will be referred to herein as "active struts." FIG. 2A shows three electrodes 117 on each of the active struts.

Different embodiments may include various numbers of struts, and in each of those embodiments all or a subset of the struts may be active struts. In the particular embodiment shown, the catheter includes four struts 112a, 112b. Two of the struts 112a, which are circumferentially adjacent to one other, are active struts, while the others two struts 112b are not active struts. The struts 112a, 112b mechanically retain the electrode carrying member 110 within the target blood vessel and bias the electrodes 117 in contact with the vessel wall. The material forming the struts 112a,b may have a shape set or shape memory that aids in biasing the radially-outward facing surfaces (and thus the electrodes) against the vessel wall.

For certain therapeutic applications, such as those described in the patents and applications referenced in the Background section, the active struts 112a should be positioned against the posterior wall of the target vessel in order to most effectively deliver neuromodulation energy to the target nerves. The specific examples discussed in this application will be described in the context of positioning the active struts 112a against the posterior wall of the vessel, but it should be understood that the configurations and methods described here may be used to confirm other desired circumferential orientations of the electrodes.

In general, the electrode carrying member is designed to be intravascularly positioned at a target site under single-view fluroscopic imaging. By "single-view" positioning it is meant that the practitioner can obtain the needed information concerning the radial and longitudinal positioning of the catheter within the vasculature from the fluroscopic (or x-ray) image without the need to move the imaging head to two or more locations. The electrode carrying member includes features arranged so that the appearance of the features on the fluoroscopic image will allow the practitioner to determine whether the electrode carrying member 110 is positioned with the active struts 112a against the desired face of the interior vessel wall. As one example shown in FIG. 2B, the features are markers arranged in a predetermined pattern, with the pattern on one active strut 112a being different from the pattern on the other active strut 112a. Various patterns may be used for this purpose. In this specific example, the pattern comprises one marker 118a on one active strut (the upper strut in FIG. 2B), and two markers 118b on the second active strut 112a. FIGS. 2C and 2D schematically depict the arrangement of the marks as seen on the fluroscopic image (in this case the AP view) when the electrodes are positioned against the anterior and posterior wall of the target vessel V, respectively. When the electrodes are against the anterior wall, the pair of markers 118b on a common strut appear at the top of the image while the single marker 118a appears at the bottom. However when the electrodes are against the posterior wall, the pair of markers 118b on the common strut appear at the bottom of the image while the single marker 118a appears at the top. In other words, if the active struts are against one face of the vessel the arrangement of markers appears in a first pattern, but if the active struts are against the opposite face the arrangement of markers appears in a second pattern that is inverted (relative to the first pattern) about the longitudinal axis of the electrode carrying member.

When the catheter is being positioned for use in performing therapies best performed with the electrodes against the posterior wall (such as the therapies described in the applications referenced in the Background), the practioner would, upon seeing the markers arranged as shown in FIG. 2C on the fluroscopic display, rotate the electrode carrying member about its longitudinal axis (e.g. by torquing the catheter within the vessel) until the markers are arranged as shown in FIG. 2D.

In the FIG. 2B embodiment, the markers 118a, 118b are disposed longitudinally adjacent to the electrodes on the corresponding strut. This allows the practitioner to see the proximal and distal extents of the array of electrodes 117 when selecting the target site for the electrode carrying member 110 along the length of the vessel. As discussed above, practitioners may choose the longitudinal positions of the electrodes within the vessel based on reference anatomy visible under fluoroscopy. Additionally, in this embodiment the markers 118a, 118b may take the form of radiopaque (e.g. tungsten-doped) rivets that perform the additional function of securing a flex circuit (on which the electrodes are formed) onto the corresponding strut. Examples of such rivets and methods of using them to assemble the catheter assembly are described in U.S. application Ser. No. 16/712,936_(Ref: NTK2-2010), entitled Medical Electrodes Using Flexible Circuits, and Methods of Manufacturing, filed Dec. 12, 2019, which is incorporated herein by reference. Although three such rivet markers 118a, 118b are shown in FIG. 2B embodiment, a fourth rivet 120 that is radiolucent so it does not appear on the fluroscopic image is used to secure the flex circuit in the area of the corresponding strut where no marker is used. In alternative embodiments, rivet 120 may be replaced by a rivet that is radiopaque to a greater or lesser extent than the other rivets so that on the fluoro image it appears more or less bright than the markers 118a, 118b.

In general, embodiments incorporating aspects of the present invention may define the fluoroscopically features using a variety of different types of material visible under fluoroscopy. Exemplary materials include, but are not limited to radiopaque gold or platinum, or polymers such as tungsten filled or doped polymers.

FIGS. 3-10 illustrate alternative features visible in the fluroscopic image that may be used to determine the rotational orientation of the electrode carrying member. As with the first embodiment, the fluoroscopically visible features additionally allow the practitioner to determine the proximal and distal extents of the array of electrodes 117 when selecting the target site for the electrode carrying member 110 along the length of the vessel. In each of FIGS. 3-10, the feature(s) or marker(s) shown at the top of the figure are disposed on a first one of the active struts, while the feature(s) marker(s) shown at the bottom of the figure are disposed on a second active strut. The arrangement or pattern of the illustrated features appears as shown in the drawing when the active struts are disposed against one face of the vessel (e.g. posterior or anterior), and will appear inverted along the longitudinal axis of the catheter (indicated by the dashed line in FIG. 3) when the active struts are disposed against the opposed face of the vessel.

Where the fluorscopically-visible features are markers, the marker patterns may be formed in a variety of ways. In FIG. 3, the markers shown as white in the drawing are markers made to have greater x-ray absorption than the markers shown as black, so that they appear brighter in the fluroscopic image than the markers depicted in the drawing as black.

In FIG. 4, the markers on a first strut have a different combination of shapes and/or sizes than the markers on a second strut. In FIG. 5, the markers on the first and second strut have markers that are identical but differ in numbers.

FIGS. 6-10 illustrate active struts 112a with further embodiments of feature/marker patterns or configurations.

In FIG. 6, the markers 118 are formed using heat shrink material applied to the struts 112a, with the markers on the first strut possessing different absorption properties than those on the second strut (so they appear more or less bright on the image compared with those on the second strut), and/or with the markers on the first and second struts having different sizes, patterns, or numbers. In FIG. 7, the markers 118 are formed on bands on the nitinol struts, with the first strut having markers that are different in size and/or number and/or absorption properties than those on the second strut.

FIG. 8 depicts the use of flurosopically-visible features, where the features are the first and second struts themselves. One of the struts (the lower strut in the drawing) absorbs more x-rays than the other strut so it appears brighter on the image. The struts, or a covering on the struts, may be made of polymeric material to provide the appropriate absorption characteristics. FIG. 9 depicts the use of struts visible on the fluroscopic image (e.g. struts formed of polymeric material or another radiopaque material) where the fluroscopically-visible features/markers are holes formed in the radiopaque struts. The first strut may have holes that differ in number, shape, pattern, and/or size than the holes on the second strut. The struts shown in FIG. 10 include tantalum markers swaged into nitinol struts. As with the rivets described in connection with the FIG. 2B embodiment, these may service the additional function of retaining the flex circuit on which the electrodes are formed onto the struts.

While the application describes several embodiments in which the fluroscopically-visible features are positioned on the active struts, in alternative embodiments these struts can be in other positions, such as on the non-active struts.

FIGS. 11A and 11B illustrate the distal tip 116 of an electrode carrying member. The tip's marking 112, when viewed on the fluoroscopic image, has a first shape (FIG. 11A) when the electrode carrying member is in a first radial orientation, but a second shape (FIG. 11B) when the electrode carrying member is in a second orientation. Similarly, as depicted in FIGS. 12A and 12B, the marker 124 on the electrode carrying member may, when within the vessel V and viewed on the fluoro image, show a first aspect ratio when it is in a first radial orientation, and a second aspect ratio (FIG. 12B) when it is in a second radial orientation. In the FIG. 11A-12B embodiments, the second radial orientation may be rotationally offset from the first radial orientation by 90 or 180 degrees, or by some other degree of rotation.

All patents and applications referred to in this application, including for purposes of priority, are incorporated herein by references.

I claim:

1. An electrode catheter for intravascular therapeutic use, the electrode catheter comprising:
    a support;
    an electrode-carrying member on the support, the electrode-carrying member including longitudinally extending first and second struts positionable in a blood vessel;
    electrodes on the electrode-carrying member; and
    a first arrangement of fluoroscopically visible features on the first strut, and a second arrangement fluoroscopically visible features on the second strut, wherein fluoroscopically visible features of the first arrangement differ from fluoroscopically visible features of the second arrangements in at least one of shape, size and brightness so that the appearance of the fluoroscopically visible features on a single-view fluoroscopic image changes with the rotational orientation of the electrode carrying member.

2. The electrode catheter of claim 1, wherein each of the first and second arrangements includes one or more markers, the markers of the first arrangement differing in shape from the markers of the second arrangement.

3. The electrode catheter of claim 1, wherein each of the first and second arrangements includes one or more markers, the markers of the first arrangement differing in size from the markers of the second arrangement.

4. The electrode catheter of claim 1, wherein each of the first and second arrangements includes one or more markers, the markers of the first arrangement differing in brightness on the fluoroscopic image compared with the markers of the second arrangement.

5. The electrode catheter of claim 1, wherein the markers of the first arrangement further differ in pattern from the markers of the second arrangement.

6. The electrode catheter of claim 5, wherein the first arrangement includes a pattern of one or more markers, and wherein the second arrangement includes a larger number of markers than the first arrangement.

7. The electrode catheter of claim 1, wherein the fluoroscopically visible feature has a first appearance when the electrodes are positioned against a posterior wall of the blood vessel, and a second, different, appearance when the electrodes are positioned against an anterior wall of the blood vessel.

8. An electrode catheter for intravascular therapeutic use, the electrode catheter comprising:
    a support;
    an electrode-carrying member on the support, the electrode-carrying member including a strut positionable in a blood vessel;
    electrodes formed on a flex circuit, the flex circuit; and
    at least one fluoroscopically visible feature on the electrode carrying member, the at least one fluoroscopically visible feature arranged so that the appearance of the fluoroscopically visible feature on a single-view fluoroscopic image changes with the rotational orientation of the electrode carrying member,
    wherein the fluoroscopically visible feature connects the flex circuit to the strut.

9. The electrode catheter of claim 8, wherein the electrodes are formed on flex circuits, and wherein the fluoroscopically visible features include rivets coupling the flex circuits to the struts.

10. The electrode catheter of claim 8, wherein the electrodes are formed on flex circuits, and wherein the fluoroscopically visible features include swages coupling the flex circuits to the struts.

11. The electrode catheter of claim 8, wherein the fluoroscopically visible feature has a first appearance when the electrodes are positioned against a posterior wall of the blood vessel, and a second, different, appearance when the electrodes are positioned against an anterior wall of the blood vessel.

12. An electrode catheter for intravascular therapeutic use, the electrode catheter comprising:
    a support;
    an electrode-carrying member on the support, the electrode-carrying member positionable in a blood vessel;
    electrodes on the electrode-carrying member; and
    a fluoroscopically visible feature on the electrode carrying member, the fluoroscopically visible feature arranged so that the appearance of the fluoroscopically visible feature on a single-view fluoroscopic image changes with the rotational orientation of the electrode carrying member, wherein the fluoroscopically visible feature has a first shape visible in the fluoroscopic view when the electrode catheter is in a first rotational orientation, and a second, different, shape visible in the fluoroscopic view when the electrode catheter is in a second rotational orientation.

13. The electrode catheter of claim 12, wherein the fluoroscopically visible feature has a first aspect ratio visible in the fluoroscopic view when the electrode catheter is in a first rotational orientation, and a second, different, aspect ratio visible in the fluoroscopic view when the electrode catheter is in a second rotational orientation.

14. The electrode catheter of claim 13, wherein the fluoroscopically visible feature is in a tip of the electrode catheter.

15. The electrode catheter of claim 12, wherein the fluoroscopically visible feature has a first appearance when the electrodes are positioned against a posterior wall of the blood vessel, and a second, different, appearance when the electrodes are positioned against an anterior wall of the blood vessel.

* * * * *